United States Patent
Sakamoto

(10) Patent No.: US 10,898,140 B2
(45) Date of Patent: Jan. 26, 2021

(54) TOMOGRAPHIC IMAGE FORMING APPARATUS AND CONTROL METHOD

(71) Applicant: TERUMO KABUSHIKI KAISHA, Tokyo (JP)

(72) Inventor: Masayuki Sakamoto, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 980 days.

(21) Appl. No.: 15/466,911

(22) Filed: Mar. 23, 2017

(65) Prior Publication Data
US 2017/0224286 A1   Aug. 10, 2017

Related U.S. Application Data

(63) Continuation of application No. PCT/JP2015/077172, filed on Sep. 25, 2015.

(30) Foreign Application Priority Data

Sep. 26, 2014   (JP) .................................. 2014-197500

(51) Int. Cl.
*A61B 5/00*   (2006.01)
*A61B 1/00*   (2006.01)
(Continued)

(52) U.S. Cl.
CPC .............. *A61B 5/7225* (2013.01); *A61B 1/00* (2013.01); *A61B 5/0066* (2013.01);
(Continued)

(58) Field of Classification Search
CPC . A61B 5/0066; A61B 5/0073; A61B 5/02007; A61B 5/0275; A61B 5/6852;
(Continued)

(56) References Cited

U.S. PATENT DOCUMENTS

2013/0041218 A1   2/2013   Iida et al.
2013/0208968 A1*  8/2013   Hanebuchi ........... A61B 5/0066
                                                       382/131

FOREIGN PATENT DOCUMENTS

JP   2011-209061 A   10/2011
JP   2013-34753 A    2/2013
(Continued)

OTHER PUBLICATIONS

International Search Report (PCT/ISA/210) dated Dec. 22, 2015, by the Japanese Patent Office as the International Searching Authority for International Application No. PCT/JP2015/077172.

*Primary Examiner* — Boniface N Nganga
(74) *Attorney, Agent, or Firm* — Buchanan Ingersoll & Rooney PC

(57) ABSTRACT

A tomographic image forming apparatus is disclosed, which divides light output from a light source inside the apparatus into measurement light and reference light, and which generates a cross-sectional image of an imaging target, based on light intensity of interference light obtained from reflected light obtained by emitting the measurement light to the imaging target and the reference light. A second image is generated by converting a first image in which line data generated based on the light intensity and having information in a direction of a first axis which serves as a depth direction of the imaging target is arranged in a direction of a second axis, into a frequency domain. An artifact is removed or reduced by performing filtering on the second image. A third image is generated by inversely converting the processed second image into a spatial domain.

20 Claims, 6 Drawing Sheets

(51) Int. Cl.
    *A61B 5/02*     (2006.01)
    *A61B 5/0275*     (2006.01)

(52) U.S. Cl.
    CPC ........ *A61B 5/0073* (2013.01); *A61B 5/02007* (2013.01); *A61B 5/0275* (2013.01); *A61B 5/6852* (2013.01); *A61B 5/7203* (2013.01); *A61B 5/7207* (2013.01); *A61B 5/7257* (2013.01); *A61B 5/742* (2013.01); *A61B 5/7475* (2013.01); *A61B 2576/00* (2013.01)

(58) Field of Classification Search
    CPC ... A61B 5/7203; A61B 5/7207; A61B 5/7225; A61B 5/7257; A61B 5/742; A61B 5/7475; A61B 2576/00; A61B 1/00
    See application file for complete search history.

(56) References Cited

FOREIGN PATENT DOCUMENTS

WO     WO 2010/095370 A1     8/2010
WO     WO-2013128846 A1 *     9/2013   ........... A61B 5/7257

* cited by examiner

TOMOGRAPHIC IMAGE FORMING APPARATUS AND CONTROL METHOD

CROSS-REFERENCES TO RELATED APPLICATIONS

This application is a continuation of International Application No. PCT/JP2015/077172 filed on Sep. 25, 2015, which claims priority to Japanese Application No. 2014-197500 filed on Sep. 26, 2014, the entire contents of which are incorporated herein by reference.

TECHNICAL FIELD

The present disclosure relates to a tomographic image forming apparatus and a method for reducing or removing an artifact of a tomographic image obtained by using optical coherence tomography.

BACKGROUND DISCUSSION

As a method of capturing a blood vessel tomographic image by inserting a catheter into a vascular lumen, intravascular ultrasound (hereinafter, referred to as IVUS) or optical coherence tomography (hereinafter, referred to as OCT) is known. OCT includes various methods, which can capture a tomographic image rapidly by utilizing wavelength sweeping, for example. Hereinafter, apparatuses for capturing the tomographic image by utilizing interference light will be collectively referred to as an OCT apparatus (refer to Pamphlet of International Publication No. 2010/095370).

A characteristic of OCT is that OCT provides higher resolution (resolving power) than IVUS, and that OCT is excellent for use in evaluating calcification or a thrombus. In addition, an intravascular wall can be observed in detail. Accordingly, it is expected that OCT is applied to evaluation after stent treatment.

SUMMARY

However, if an artificial object such as a stent is present inside a blood vessel, an artifact (also referred to as noise) is caused to appear on a tomographic image due to the presence of the artificial object. For example, if a surface of a stent strut having high light reflectance is exposed to OCT measurement light, intensive reflected light (scattered light) returns. Consequently, a radial streak appears thereon. This artifact can hinder diagnosis using the tomographic image. Moreover, the artifact blocks a line of sight when a three-dimensionally reconstructed image is observed from the tomographic image. In addition, it is conceivable that the artifact will affect a process for automatically detecting the stent strut.

The present disclosure is made in view of the above-described problems, and an object thereof is to reduce or remove an artifact on a tomographic image.

According to an aspect of the present disclosure, in order to achieve the above-described object, a tomographic image forming apparatus is disclosed, which divides light output from a light source inside the apparatus into measurement light and reference light, and which generates a cross-sectional image of an imaging target based on light intensity of interference light obtained from reflected light obtained by emitting the measurement light to the imaging target and the reference light. The tomographic image forming apparatus includes first generation means for generating a second image by converting a first image in which line data generated based on the light intensity and having information in a direction of a first axis which serves as a depth direction of the imaging target is arranged in a direction of a second axis, into a frequency domain, first reduction means for removing or reducing an artifact by performing filtering on the second image, and second generation means for generating a third image by inversely converting the second image processed by the first reduction means, into a spatial domain.

In accordance with an exemplary embodiment, a tomographic image forming apparatus is disclosed which divides light output from a light source inside the apparatus into measurement light and reference light, and which generates a cross-sectional image of an imaging target based on light intensity of interference light obtained from reflected light obtained by emitting the measurement light to the imaging target and the reference light, comprising: a processor configured to: generate a second image by converting a first image in which line data generated based on the light intensity and having information in a direction of a first axis which serves as a depth direction of the imaging target is arranged in a direction of a second axis, into a frequency domain; remove or reduce an artifact by performing filtering on the second image; and generate a third image by inversely converting the second image into a spatial domain.

In accordance with another exemplary embodiment, a control method of a tomographic image forming apparatus is disclosed which divides light output from a light source inside the apparatus into measurement light and reference light, and which generates a cross-sectional image of an imaging target based on light intensity of interference light obtained from reflected light obtained by emitting the measurement light to the imaging target and the reference light, the control method comprising: generating a second image by converting a first image in which line data generated based on the light intensity and having information in a direction of a first axis which serves as a depth direction of the imaging target is arranged in a direction of a second axis, into a frequency domain; removing or reducing an artifact by performing filtering on the second image; and generating a third image by inversely converting the second image into a spatial domain.

According to the present disclosure, it is possible to reduce or remove an artifact on a tomographic image.

Other features and advantageous effects according to the present disclosure will become apparent from the following description made with reference to the accompanying drawings. In the accompanying drawings, the same reference numerals will be given to the same or similar configurations.

BRIEF DESCRIPTION OF THE DRAWINGS

The accompanying drawings are incorporated in the description, configure a part of the description, illustrate embodiments of the present disclosure to explain principles of the present disclosure as well as describe the embodiments.

DETAILED DESCRIPTION

Figure 1:
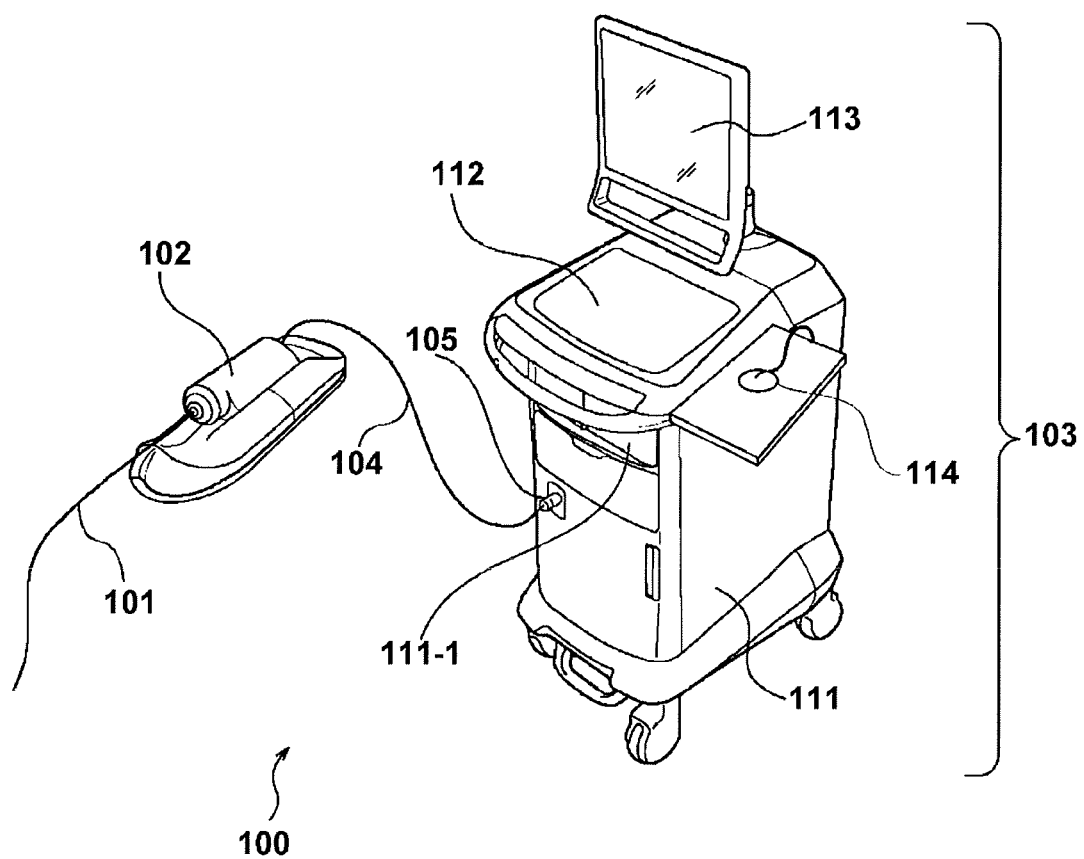
FIG. 1 is a view illustrating an external configuration of an optical imaging apparatus for diagnosis according to an embodiment.

FIG. 1 is a view illustrating an external configuration of an imaging apparatus for diagnosis 100 according to an embodiment of the present disclosure, which uses OCT (in the present embodiment, SS-OCT). As illustrated in FIG. 1, the imaging apparatus for diagnosis 100 serving as a tomographic image forming apparatus can include a probe 101, a scanner and pull-back unit 102, and an operation control device 103. The scanner and pull-back unit 102 and the operation control device 103 are connected to each other via a connector 105 by a cable 104, which accommodates a signal line and an optical fiber.

The probe 101 is directly inserted into a blood vessel. A catheter, which accommodates an imaging core can be inserted into the probe 101. The imaging core can include an optical transceiver which continuously transmits transmitted light (measurement light) to the inside of the blood vessel and which continuously receives reflected light from the inside of the blood vessel. The imaging apparatus for diagnosis 100 measures a state inside the blood vessel by using the imaging core. The probe 101 is detachably attached to the pullback unit 102, and the pullback unit 102 drives an embedded motor, thereby regulating the imaging core inside a catheter inserted into the probe 101, when the imaging core performs an operation in an axial direction and an operation in a rotation direction inside the blood vessel. In addition, the pullback unit 102 acquires the reflected light received by the optical transceiver inside the imaging core, and transmits the reflected light to the operation control device 103.

In order to perform measurement, the operation control device 103 is provided with a function for inputting various setting values and a function for displaying various blood vessel images after processing optical interference data obtained by measurement. In the operation control device 103, the reference numeral 111 represents a main body control unit. The main body control unit 111 generates interference light data by causing the reflected light from the imaging core to interfere with reference light obtained by separating light from a light source. Based on the interference light data, the main body control unit 111 generates the line data, and generates a tomographic image (blood vessel cross-sectional image) based on light interference through interpolation processing.

The reference numeral 111-1 represents a printer & DVD recorder, which prints a processing result in the main body control unit 111 or stores the processing result as data. The reference numeral 112 represents an operation panel. A user inputs various setting values and instructions via the operation panel 112. The reference numeral 113 represents an LCD monitor serving as a display device. The LCD monitor 113 displays various cross-sectional images generated by the main body control unit 111. The reference numeral 114 represents a mouse serving as a pointing device (coordinate input device).

Figure 2:
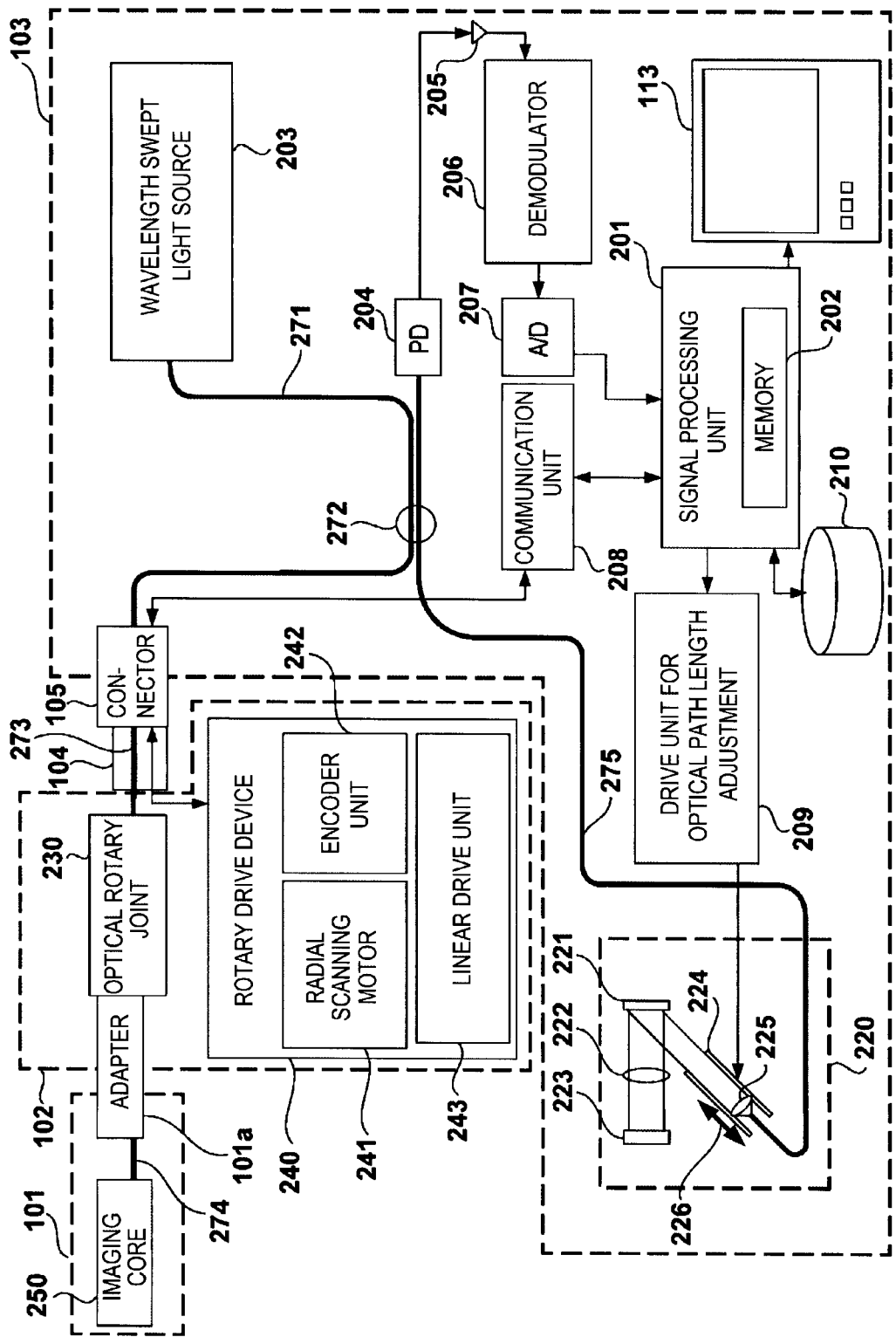
FIG. 2 is a view illustrating a functional configuration of the optical imaging apparatus for diagnosis.

Next, a functional configuration of the imaging apparatus for diagnosis 100 will be described. FIG. 2 is a block configuration diagram of the imaging apparatus for diagnosis 100. Hereinafter, referring to the drawing, a functional configuration of wavelength swept OCT (SS-OCT) will be described.

In FIG. 2, the reference numeral 201 represents a signal processing unit, which performs overall control on the imaging apparatus for diagnosis, and is configured to have some circuits including a microprocessor. The reference numeral 210 represents a non-volatile storage device represented by a hard disk, and stores various programs or data files to be executed by the signal processing unit 201. The reference numeral 202 represents a memory (RAM) disposed inside the signal processing unit 201. The microprocessor (computer) of the signal processing unit 201 executes a program stored in the memory 202, thereby performing a tomographic image generation process including reduction/ removal of an artifact (to be described later). The reference numeral 203 represents a wavelength swept light source, and represents a light source, which repeatedly generates light having a wavelength varying within a preset range along a time axis.

The light output from the wavelength swept light source 203 is incident on one end of a first single mode fiber 271, and is transmitted toward a distal side. The first single mode fiber 271 is optically coupled to a fourth single mode fiber 275 in an optical fiber coupler 272 located in an intermediate portion. In the optical fiber coupler 272, the light output from the wavelength swept light source 203 is divided into the measurement light and the reference light. The reference light proceeds to the fourth single mode fiber 275. The light (measurement light) which is incident on the first single mode fiber 271 and which is emitted to the distal side by the optical fiber coupler 272 is guided to a second single mode fiber 273 via the connector 105. The other end of the second single mode fiber 273 is connected to an optical rotary joint 230 inside the pullback unit 102.

In accordance with an exemplary embodiment, the probe 101 has an adapter 101a for being connected to the pullback unit 102. Then, the probe 101 is connected to the pullback unit 102 by the adapter 101a, thereby allowing the probe 101 to be stably held by the pullback unit 102. Furthermore, an end portion of a third single mode fiber 274, which is rotatably accommodated inside the probe 101 is connected to the optical rotary joint 230. As a result, the second single mode fiber 273 and the third single mode fiber 274 are optically coupled to each other. An imaging core 250 having the mounted optical transceiver which emits the light in a direction substantially orthogonal to a rotation axis and which receives the reflected light is disposed in the other end (leading portion side of the probe 101) of the third single mode fiber 274.

As a result of the above-described configuration, the light emitted by the wavelength swept light source 203 is guided to the imaging core 250 disposed in an end portion of the third single mode fiber 274 via the first single mode fiber 271, the second single mode fiber 273, and the third single mode fiber 274. The optical transceiver of the imaging core 250 emits the light in a direction substantially orthogonal to an axis of the fiber, and emits the measurement light to an imaging target. The optical transceiver receives the reflected light. The received reflected light is reversely guided in turn, and is caused to return to the operation control device 103.

A rotary drive device 240 has a radial scanning motor 241 which rotationally drives the imaging core and the third single mode fiber 274, an encoder unit 242 which is used for rotary drive control, and a linear drive unit 243 for linearly driving (pullback) the imaging core and the third single mode fiber 274.

In accordance with an exemplary embodiment, an optical path length changing mechanism 220 which fine-adjusts an optical path length of the reference light is disposed in an end portion opposite to the fourth single mode fiber 275 coupled to the optical fiber coupler 272. The optical path length changing mechanism 220 functions as optical path length changing means for changing the optical path length corresponding to length variations so that the length variations of the respective probes 101 can be absorbed in a case of replacing the probes 101. Therefore, a collimator lens 225 located in an end portion of the fourth single mode fiber 275 is disposed on a one-axis stage 224 which is movable in a direction indicated by an arrow 226, that is, an optical axis direction thereof.

Furthermore, the one-axis stage 224 is also provided with a function as adjusting means for adjusting offset. For example, even in a case where the distal end of the probe 101 is not in close contact with a biological tissue surface, the one-axis stage finely changes the optical path length. In this manner, a state can be set where the reflected light from a position of the biological tissue surface is interfered with the reference light.

The optical path length is fine-adjusted in the one-axis stage 224. The light reflected on a mirror 223 via a grating 221 and a lens 222 is guided again to the fourth single mode fiber 275, and is mixed with the light obtained from the second single mode fiber 273 side, in the optical fiber coupler 272. In this manner, the light is received as the interference light by a photodiode 204. The interference light received in this way by the photodiode 204 is photoelectrically converted, is amplified by an amplifier 205, and is input to a demodulator 206. The demodulator 206 performs a demodulation process for extracting only a signal component of the interfered light, and an output thereof is input to an A/D converter 207 as an interference light signal.

In the A/D converter 207, the interference light signal can be sampled as many as 2,048 points at 90 MHz, for example, thereby generating one line digital data (interference light data). A sampling frequency can be set, for example, to 90 MHz on the assumption that approximately 90% of a cycle (25 μsec) of wavelength sweeping is extracted as digital data of 2,048 points in a case where a repeated frequency of the wavelength sweeping is set to 40 kHz. However, a configuration is not particularly limited thereto.

The interference light data in line units, which is generated in the A/D converter 207, is input to the signal processing unit 201, and is temporarily stored in the memory 202. Then, in the signal processing unit 201, the interference light data is subjected to frequency decomposition by means of FFT (fast Fourier transform), data in a depth direction (hereinafter, referred to as A-line data) is generated, and the data is subjected to coordinate-convert. In this manner, an optical cross-sectional image at each position inside the blood vessel is built, and is output to an LCD monitor 113 at a predetermined frame rate. In this way, a cross-sectional image of an imaging target is generated, based on light intensity of the interference light obtained from the reflected light and the reference light. The signal processing unit 201 is further connected to a drive unit for optical path length adjustment 209 and a communication unit 208. The signal processing unit 201 performs control on a position of the one-axis stage 224 via the drive unit for optical path length adjustment 209 (optical path length control).

The communication unit 208 has some drive circuits embedded therein, and communicates with the pullback unit 102 under the control of the signal processing unit 201. Specifically, the communication unit 208 supplies a drive signal to the radial scanning motor 241 in order to cause the optical rotary joint 230 inside the pullback unit 102 to rotate the third single mode fiber 274, receives a signal from the encoder unit 242 in order to detect a rotation position of the radial motor, and supplies a drive signal to the linear drive unit 243 in order to pull the third single mode fiber 274 at predetermined speed.

The above-described process in the signal processing unit 201 is also realized by causing a computer to execute a predetermined program.

In the above-described configuration, if the probe 101 is located at a diagnosis target blood vessel position (coronary artery) of a patient, a transparent flush liquid is delivered toward the distal end of the probe 101 by a user's operation, and is discharged into the blood vessel through a guiding catheter. The reason is to exclude the blood influence. Then, if a user inputs an instruction to start scanning, the signal processing unit 201 drives the wavelength swept light source 203 so as to drive the radial scanning motor 241 and the linear drive unit 243 (hereinafter, a process of light emitting and light receiving by driving the radial scanning motor 241 and the linear drive unit 243 is referred to as scanning). As a result, wavelength swept light from the wavelength swept light source 203 is supplied to the imaging core 250 through the above-described route. In this case, while being rotated, the imaging core 250 located at a distal position of the probe 101 is moved along the rotation axis. Accordingly, while being rotated and moved along a blood vessel axis, the imaging core 250 emits the light to the vascular lumen surface, and receives the reflected light.

Figure 3:
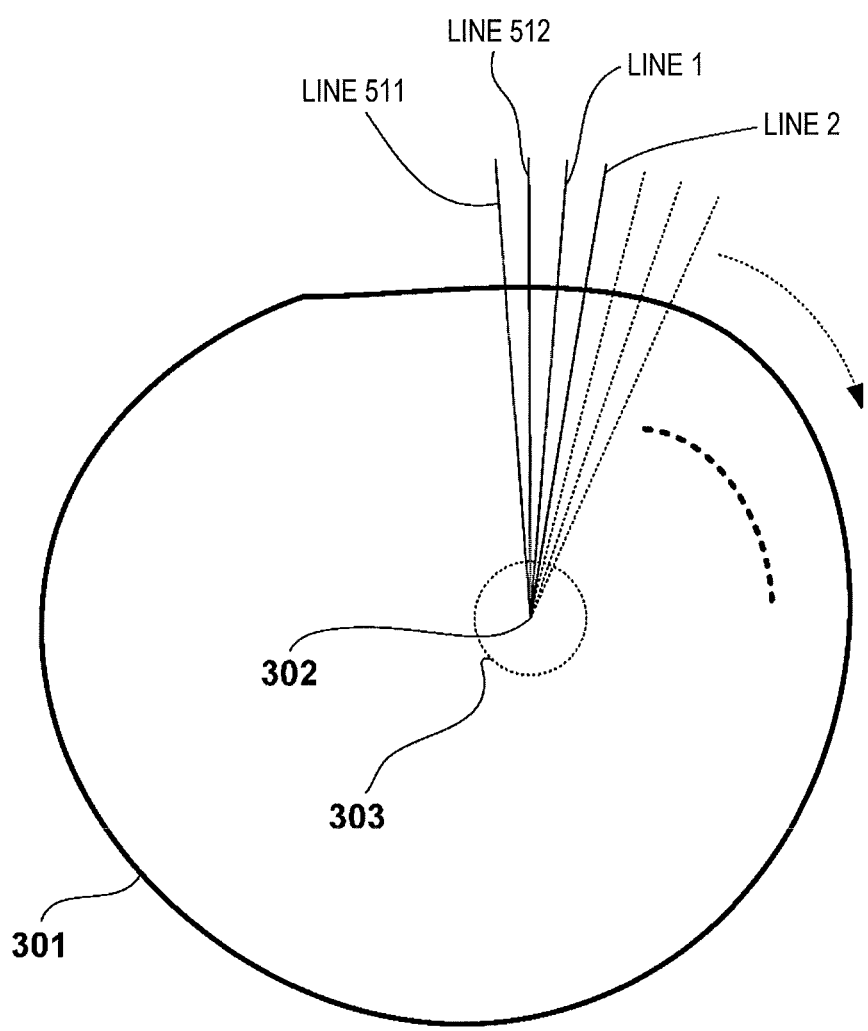
FIG. 3 is a view for describing a reconstructing process of a cross-sectional image.

Here, a process required for generating one sheet of the tomographic images (optical cross-sectional images) will be briefly described with reference to FIG. 3. The drawing is a view for describing a reconstructing process of the cross-sectional image of a vascular lumen surface 301 on which the imaging core 250 is located. While the imaging core 250 is rotated once (360 degrees), the measurement light is transmitted and received multiple times. If the light is transmitted and received once, data of one line can be obtained in the light emitting direction. Therefore, for example, during the single rotation, the light is transmitted and received 512 times. Accordingly, it is possible to obtain data of 512 lines extending radially from a rotation center 302. In the data of 512 lines, the lines are dense in the vicinity of the rotation center 302, and the lines become sparse as a distance is away from the rotation center 302. Therefore, known interpolation processing is performed to generate a pixel in an empty space between the respective lines, thereby generating a two-dimensional cross-sectional image, which is visible to humans. A center position of the two-dimensional cross-sectional image is coincident with the rotation center 302 of the imaging core 250. However, it is to be noted that the center position is not a center position of the blood vessel cross section. In addition, the light is reflected on a lens surface of the imaging core 250 or a surface of the catheter. Accordingly, as illustrated by the reference numeral 303, some circles concentric to the rotation center 302 are generated.

Figure 4:
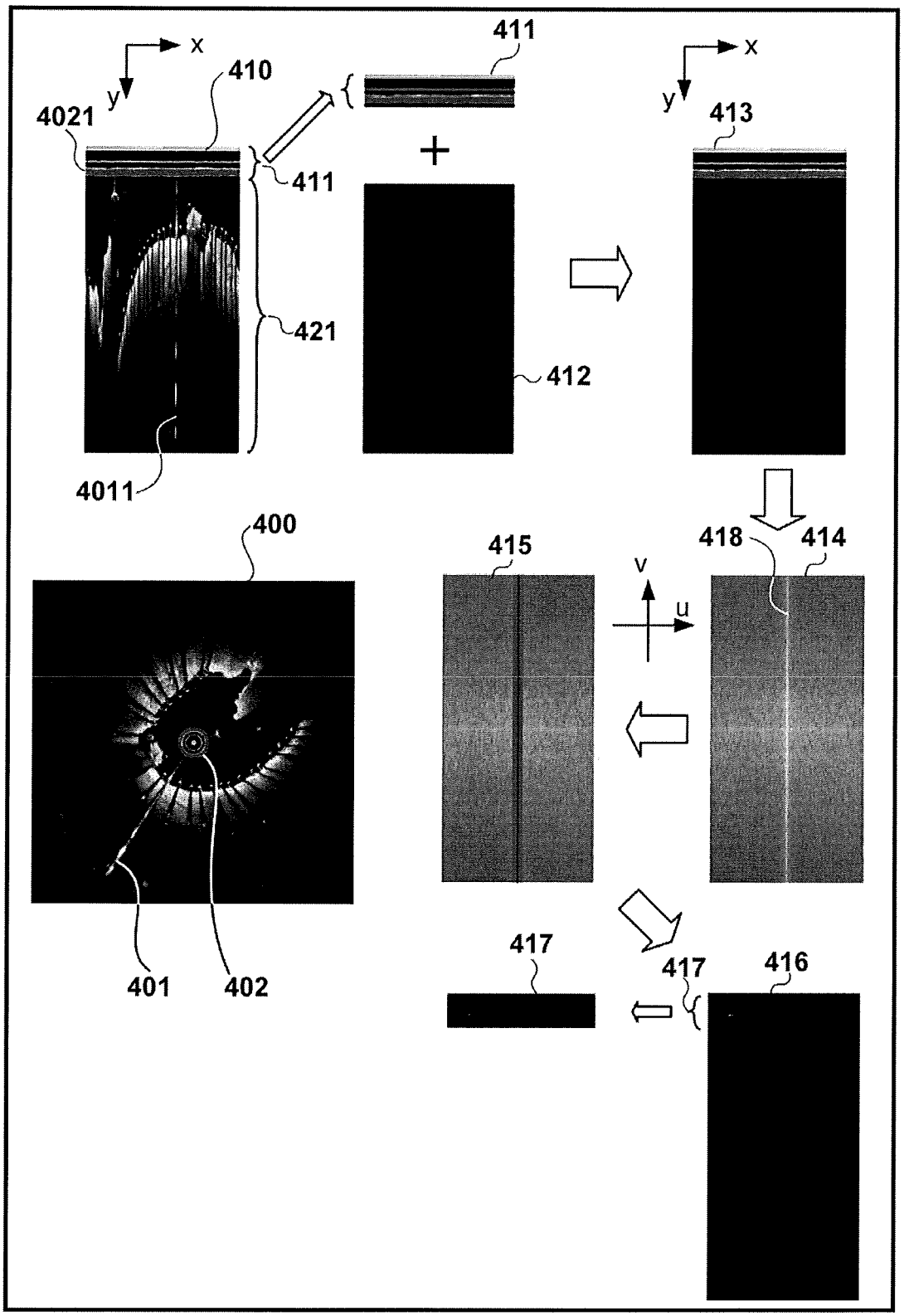
FIG. 4 is a schematic view for describing an artifact reduction process according to the embodiment.
Figure 5:
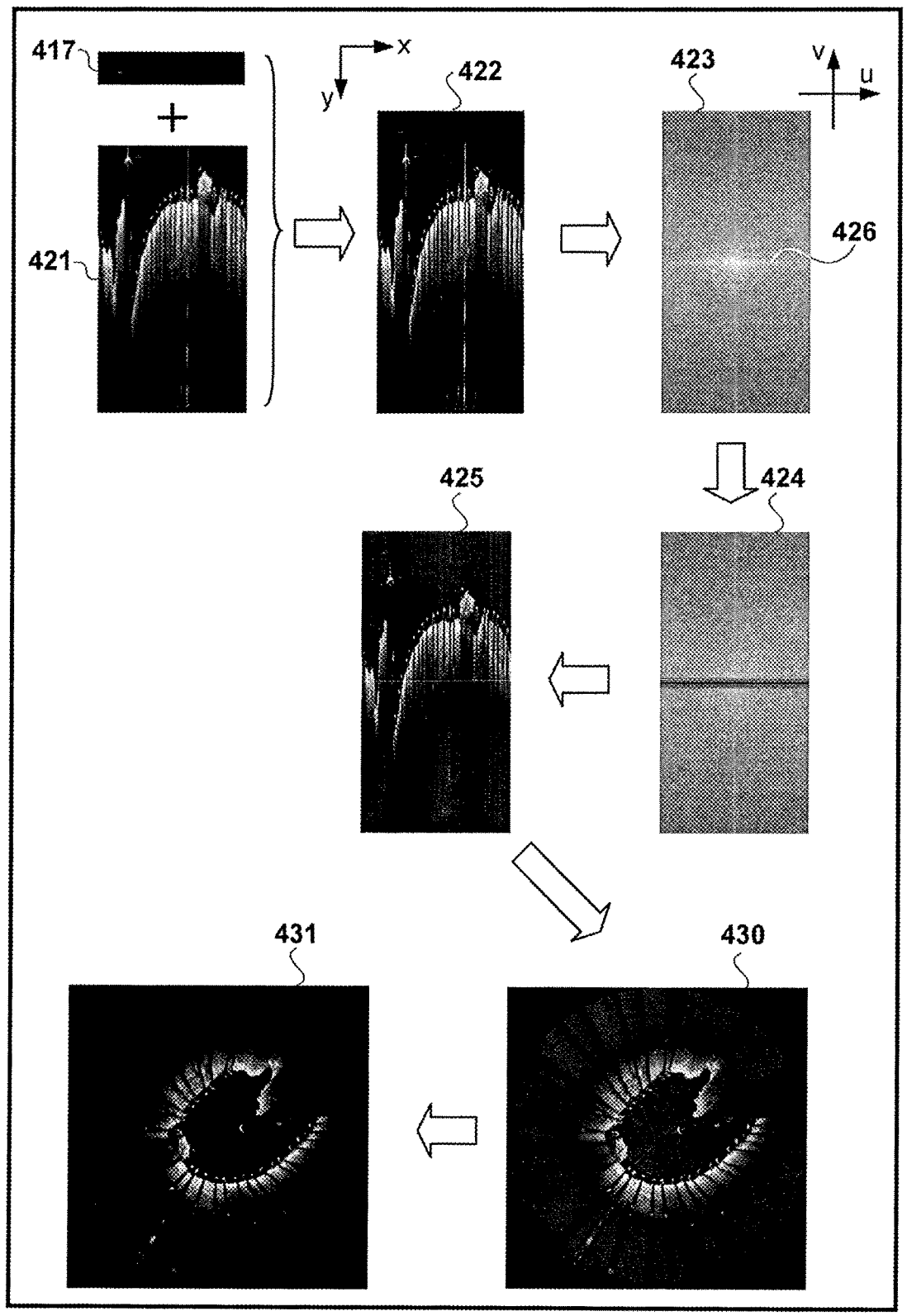
FIG. 5 is a schematic view for describing an artifact reduction process according to the embodiment.
Figure 6:
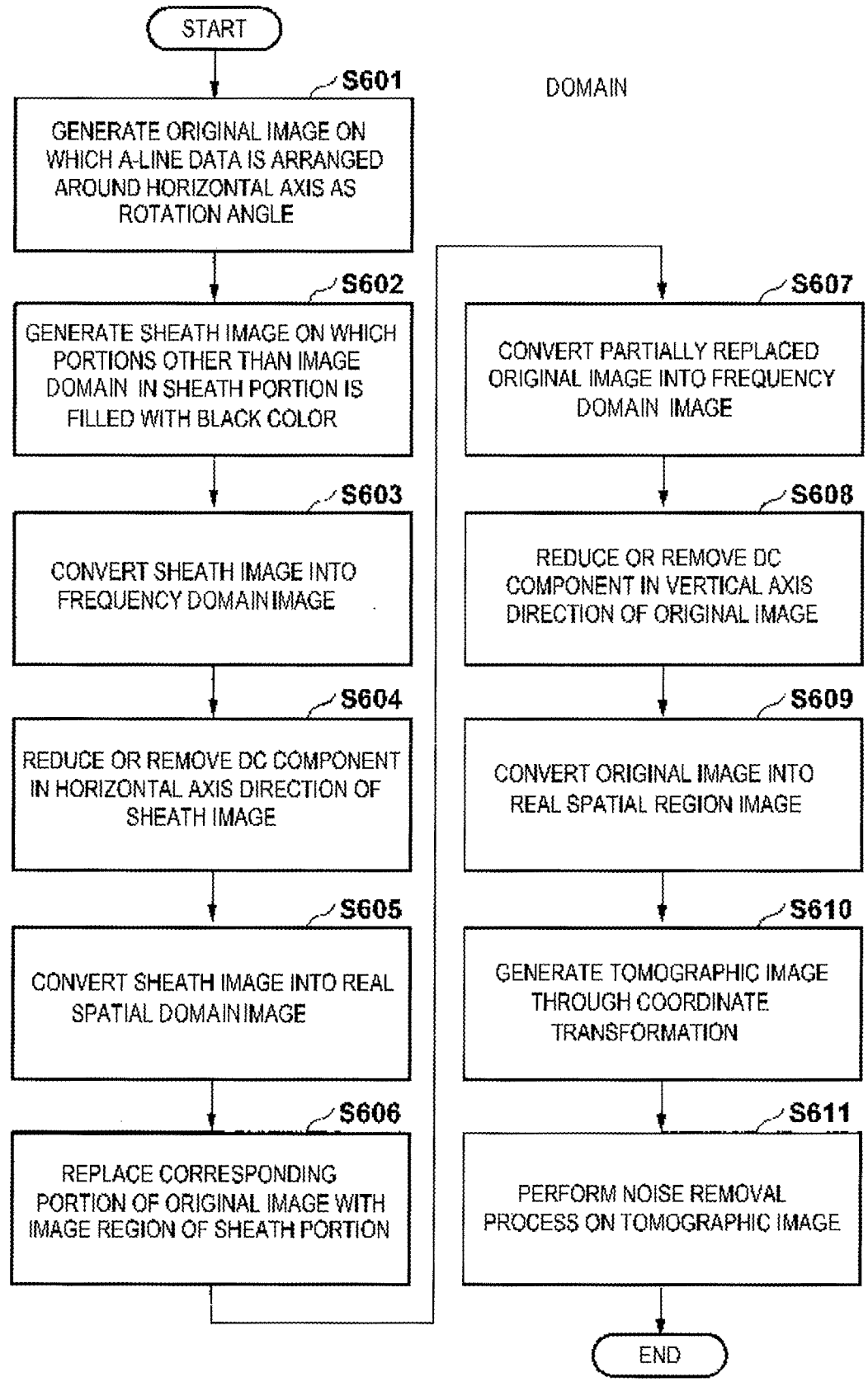
FIG. 6 is a flowchart illustrating an artifact reduction process according to the embodiment.

Next, a process for reducing the artifact on the tomographic image obtained as described above will be described with reference to FIGS. 4 to 6. FIGS. 4 and 5 are schematic views for describing the artifact reduction process according to the embodiment. FIG. 6 is a flowchart illustrating the artifact reduction process according to the embodiment, which is realized by causing the microprocessor (computer) of the signal processing unit 201 to execute a program stored in the memory 202. A case will be described where a tomographic image 400 is obtained according to the above-described configuration. A radial artifact 401 caused by the reflection of the stent strut appears on the tomographic image 400. In addition, a concentric ring-shaped artifact 402 appears in a central portion on the tomographic image 400 due to the reflection on the lens surface, an inner surface, or an outer surface of the catheter sheath or an optical system. In the artifact removal process according to the present embodiment, this radial artifact 401 is effectively reduced or removed.

As described with reference to FIG. 3, the tomographic image 400 is obtained by radially arranging the A-line data around the rotation center 302. As described above with reference to FIG. 3, the A-line data configures the tomographic image obtained by rotating the light emitted from the imaging core 250 360 degrees through the optical coherence tomography, and is obtained in each emitting direction. In the present embodiment, the artifact is reduced using an original image 410 obtained by arranging this A-line data in a horizontal axis direction (x-axis direction) as a rotary angle. Therefore, first, in Step S601, the signal processing unit 201 arranges the A-line data, which are obtained in the emitting directions, in the horizontal axis direction (x-axis direction) as the rotary angle, thereby obtaining the original image 410. A vertical axis direction (y-axis direction) on the original image 410 is coincident with the direction of the A-line data, and an upper side is coincident with the rotation center 302 of each A-line data. As illustrated in the original image 410, the concentric ring-shaped artifact 402 on the tomographic image 400 becomes a line 4021 in the x-axis direction, and the artifact 401 extending radially on the tomographic image 400 becomes an artifact 4011 extending in the y-axis direction.

The subsequent process in Steps S602 to S606 is performed in order to remove an image (that is, the line 4021) of the lens surface or the catheter sheath, which appears substantially concentrically on the tomographic image 400. This can help reduce the influence of the line 4021 for the removal process of the artifact 4011 (to be described later). First, in Step S602, the signal processing unit 201 selects a predetermined region on the rotation center side of the A-line data in the original image 410 on which the A-line data is arranged in the horizontal axis direction. The predetermined region is a region where the line 4021 is present on the original image 410 (hereinafter, this region is referred to as a sheath region 411). The sheath region 411 may be selected (extracted) from the original image 410 so that a user designates a boundary of the sheath region 411 while observing the original image 410. Alternatively, the positions of the inner wall and the outer wall of the catheter sheath can be, to some extent, determined from the lens surface in the imaging core. Accordingly, a region within a predetermined distance from the rotation center may be extracted as the sheath region 411 so as to automatically include the tube walls of the catheter sheath.

Next, in Step S602, the signal processing unit 201 cuts out an image of the sheath region 411 from the original image 410, and generates a sheath image 413 by connecting the image to a black image 412 having the same size as that of a non-sheath region 421 which is an image region other than the sheath region 411. The sheath image 413 may be generated and acquired in such a way that the region other than the sheath region 411 (non-sheath region 421 which is the region other than the above-described predetermined region) on the original image 410 is filled with a black color (lowest brightness value). Alternatively, an image of the sheath region 411 may be cut out so as to be used for the following process as the sheath image 413.

Next, in Step S603, the signal processing unit 201 converts the sheath image 413 which is a spatial domain image into a frequency domain image 414. As a method of converting the spatial image into the frequency domain image, a known converting method can be used, such as two-dimensional Fourier transform, cosine transform, and sine transform. The frequency domain image 414 illustrated in FIG. 4 is obtained through logarithmic representation of amplitude in the two-dimensional Fourier transform, and is shifted so that a DC component is an image center. On this image 414, a u-axis direction represents frequency distribution in the x-axis direction on the sheath image 413, and a v-axis direction represents frequency distribution in the y-axis direction on the sheath image 413. An image extending in the x-axis direction on the original image 410 in the spatial domain as the line 4021 has zero or approximate zero frequency component in the x-axis direction, and is mainly expressed by the frequency component in the y-axis direction. Therefore, the line 4021 appears as an image 418 extending in the v-axis direction near u=0, on the frequency domain image 414.

In Step S604, the signal processing unit 201 performs a process for removing or reducing the sheath image extending in the x-axis direction. Here, in order to relatively reduce the amplitude of the DC component, which shows a zero frequency on the image 414, compared to other components, the following process is performed, for example. On the image 414, the signal processing unit 201 performs a filtering process in which values of some or all of the lines u=0 which show the DC component (zero frequency component) in the u-axis direction or values in the vicinity of the lines (−Δu≤u≤Δu) decrease to zero or smaller, or gradually approximate to zero, thereby generating a processed image 415. Subsequently, in Step S605, the signal processing unit 201 performs a process for returning the processed image 415 to the spatial domain image 416. For example, if the processed image 415 is an amplitude image in the frequency space, which is obtained through the Fourier transform process, the processed image 415 is subjected to the inverse Fourier transform in conjunction with a phase image. In this manner, the spatial domain image 416 is obtained. In some cases, the artifact 401 extending radially extends into the sheath region 411. Therefore, in order to remove the artifact, filtering may be further performed in which the zero frequency component (line of v=0) in the horizontal axis direction decreases to zero or smaller, or gradually approximates to zero.

Subsequently, in Step S606, the signal processing unit 201 cuts out a region corresponding to the sheath region 411 as an image 417 from the image 416, and replaces the sheath region 411 of the original image 410 with the image 417. In this way, an image 422 is obtained in which the sheath image is removed/reduced from the original image 410. For example, the image 417 cut out from the image 416 and the image of the non-sheath region 421 obtained from the original image 410 are connected to each other, thereby obtaining the image 422 (partially replaced original image) in which the sheath image is removed from the original image 410. A method of generating the image 422 is not limited to the above-described one. For example, the image 422 may be generated in such a way that a position corresponding to the sheath region 411 of the original image 410 is overwritten with the image 417.

Subsequently, in Steps S607 to S609, the removal process is performed on the artifact 401 (4011) extending radially. First, in Step S607, the signal processing unit 201 converts the image 422 in which the sheath image is removed/reduced (partially replaced original image), into a frequency domain image 423. The process in Step S607 is similar to the process in Step S603. As a method of converting the spatial domain image into the frequency domain image, a known converting method can be used, such as two-dimensional Fourier transform, cosine transform, and sine transform.

As described above, the artifact 401 appears as an image (artifact 4011) extending long in the vertical direction (y-axis direction) on the image 422. Therefore, in Step S608, the signal processing unit 201 removes or reduces the artifact in the vertical direction on the image 422. Here, in order to relatively reduce the amplitude of the DC component, which shows a zero frequency on the image 423, compared to other components, the following process is performed, for example. On the frequency domain image 423, the artifact extending in the vertical direction on the image 422 appears as an image 426 extending in the u-axis direction near v=0. Therefore, in the process for removing or reducing the DC component in Step S608, the signal processing unit 201 performs a filtering process in which values of some or all of the lines v=0 which show the DC component (zero frequency component) corresponding to the artifact in the y-axis direction on the image 422 or values in the vicinity of the lines (−Δv≤v≤Δv) decrease to zero or smaller, or gradually approximate to zero, thereby generating a processed image 424.

In some cases, a ring-shaped artifact can appear on the tomographic image 400 due to the reflection on the lens surface, an inner surface, or an outer surface of the catheter sheath or an optical system in the imaging core. In a case where filtering is performed on u=0 or the vicinity values concurrently with the process on the line v=0, the process is also concurrently performed on the ring-shaped artifact. However, the process may not necessarily be performed concurrently. Therefore, in order to remove the artifact, filtering may be further performed in which a value of some or all of the lines u=0 which show the DC component (zero frequency component) in the u-axis direction or values in the vicinity of the lines (−Δu≤u≤Δu) decrease to zero or smaller, or gradually approximate to zero. In addition, another filtering may be performed so as to remove the noise.

Subsequently, in Step S609, the processed image 424, which is the frequency domain image is converted into a spatial image. For example, if the processed image 415 is an amplitude image in the frequency space, which is obtained through the Fourier transform, the processed image 415 is subjected to the inverse Fourier transform in conjunction with a phase image. In this manner, a spatial domain image 425 is obtained. Then, in Step S610, the signal processing unit 201 performs coordinate-convert on the image 425, thereby generating a tomographic image 430. That is, the signal processing unit 201 radially re-arranges the A-line data for the respective rotation positions (θ) configuring the image 425, and performs interpolating between lines, thereby generating the tomographic image 430.

The tomographic image 430 can be obtained in which the artifact is removed or reduced as described above. However, in some cases, noise is generated on the tomographic image 430 through the process for the above-described frequency domain image. Therefore, in Step S611, a noise removal process is further performed on the tomographic image 430. For example, this noise removal process can be realized by applying a known filter such as a Gaussian filter, a local average filter, and a median filter to the tomographic image 430 in the spatial domain. Alternatively, a threshold process using a brightness threshold and an area threshold may be performed. During the threshold process, in a case where the tomographic image 430 is binarized (in black and white) using the brightness threshold, adjacent white pixels can be united into one. In a case where an area thereof is equal to or smaller than the area threshold, a process for deleting the united pixels (black coloring) is performed. For example, as the brightness threshold, a value of 5% to 30% (more preferably 5% to 20%) of the upper limit brightness value is used. For example, as the area threshold, 0.006 mm$^2$ (more preferably 0.004 mm$^2$) is used.

The filtering process and the threshold process, which are known may be combined with each other. During the threshold process, any one or both of the brightness threshold and the area threshold may be used. In addition, in the spatial domain, the known filtering process or the threshold process is performed on the tomographic image 430. However, without being limited thereto, the known filtering process or the threshold process may be performed on the image 425 obtained before the coordinate-convert. In addition, one of the filtering process and the threshold process may be performed before the coordinate-convert, and the other may be performed after the coordinate-convert.

In addition, during the noise removal process in Step S611, the tomographic image 430 may be converted into the frequency domain image. A predetermined process may be performed on the frequency domain image, and the processed image may be returned to the spatial domain image. In this manner, the noise may be removed. For example, the predetermined process performed on the frequency domain image can include using a high-pass filter, particularly, a filter for decreasing the DC component to zero or smaller or for causing the DC component to gradually approximate to zero, or a low-pass filter. In addition, the process in the above-described spatial domain and the process in the frequency domain may be combined with each other. Furthermore, the above-described threshold process may be performed on the frequency domain image.

In Steps S604 and S608, the following filter may be used for the amplitude image in the frequency domain. That is, the filter has a distribution in which a center of a region, which has a predetermined width from a line extending in a direction in which the vertical axis or horizontal axis DC component is arranged, is decreased to zero or smaller or gradually approximated to zero, and both ends of the predetermined width (for example, −Δu to Δu or −Δv to Δv) are gradually approximated to original values.

In addition, in the filtering performed on the image obtained by being converted into the frequency domain, without being limited to the above-described filtering process, for example, a known filtering process using a Wiener filter or a high boost filter may be performed.

Various filtering processes are performed. However, for example, in a case where the filtering is performed in order to decrease the DC component to zero in the frequency domain, the tomographic image 430 or the tomographic image 431, which is finally generated becomes darker than the image generated without removing the artifact. Accordingly, brightness correction may be performed concurrently with or after the filtering. The brightness correction may be performed in the frequency domain, or may be performed in the spatial domain. In addition, the brightness correction may be performed after each filtering process, and may be performed only after the final filtering process. The number or the procedure of the brightness correction processes do not matter.

In addition, for example, the brightness correction may be performed using a tone curve. For example, in a case where the brightness correction is performed in the frequency domain, the maximum value of the amplitude image may be stored in advance. The tone curve may be set so that the maximum value obtained after the filtering is performed on the DC component is the maximum value before the filtering. Without being limited to a linear shape, the tone curve may not be the linear shape. Furthermore, the tone curve may not pass through an origin.

In addition, even in a case where the brightness correction is performed in the spatial domain, the brightness correction may be performed similarly to the case where the brightness correction is performed in the frequency domain. However, in the brightness correction performed in the spatial domain, without being limited to the maximum value, a tone curve may be set so that a change in the brightness value of a certain interest point is close to zero. In this case, the interest point may be set at multiple locations. The tone curve may be subjected to least square approximate through polynomial expression. The interest point may be set by detecting a characteristic on an image such as the stent strut, may be fixed in advance, or may be manually set. In addition, the interest point may be set in combination thereof.

In addition, as the original image 410, the above-described embodiment employs an image obtained by arranging the A-line data for generating one tomographic image in the horizontal axis direction (x-axis direction) as the rotary angle, that is, an image obtained by arranging the A-line data corresponding to 360 degrees. However, a method according to the present embodiment is not limited thereto. That is, the A-line data configuring the original image 410 may be larger or smaller than 360 degrees. However, when the tomographic image is prepared in Step S610, the A-line data needs to be adjusted to line data corresponding to one tomographic image (360 degrees).

In addition, in the above-described embodiment, a case of OCT/OFDI which can obtain a cross-sectional image of the blood vessel while rotating in the vascular lumen has been described. However, without being limited thereto, as a method according to the present embodiment, substantially linear or substantially plane scanning, or successive scanning on a fixed point may be used. In this case, Step S610 is omitted.

As described above, according to the above-described embodiment, a radial artifact or a ring-shaped artifact which appears on the tomographic image by using the optical coherence tomography is removed or reduced, thereby providing the tomographic image which facilitates diagnosis. In addition, since the tomographic image is used, automatic detection of the stent strut can be more accurately performed. In addition, in the above-described embodiment, a case has been described where the microprocessor (computer) of the signal processing unit 201 executes the program stored in the memory 202 so as to realize the tomographic image generation process including the reduction/removal of the artifact and so as to output the generated image to the LCD monitor 113 for display. However, without being limited thereto, the tomographic image may be generated as image data. The generation process may be progressively performed by executing the program without displaying the image. In this case, only an image whose artifact is completely reduced/removed is output to and displayed on the LCD monitor 113. In addition, without the image whose artifact is completely reduced/removed being output to and displayed on the LCD monitor 113, the data may be stored as the image data in the storage device 210. That is, it is apparent that the image described in the above-described embodiment can include two meanings of both an image as display data output to and displayed on the LCD monitor 113 and data sequence as non-display data, which is not displayed on the LCD monitor 113.

The detailed description above describes a tomographic image forming apparatus and a method for reducing or removing an artifact of a tomographic image obtained by using optical coherence tomography. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A tomographic image forming apparatus which divides light output from a light source inside the apparatus into measurement light and reference light, and which generates a cross-sectional image of an imaging target based on light intensity of interference light obtained from the reference light and reflected light obtained by emitting the measurement light to the imaging target, comprising:
   a processor configured to:
      generate a second image by converting into a frequency domain a first image in which line data being generated based on the light intensity and having information in a direction of a first axis showing a depth direction of the imaging target is arranged in a direction of a second axis;
      remove or reduce an artifact by performing filtering on the second image; and
      generate a third image by inversely converting the second image into a spatial domain.

2. The tomographic image forming apparatus according to claim 1, wherein the first image is converted into the second image by Fourier transform, cosine transform, or sine transform.

3. The tomographic image forming apparatus according to claim 1, wherein the processor is configured to:
   reduce an amplitude of a DC component which shows a zero frequency on the second image, compared to other components.

4. The tomographic image forming apparatus according to claim 1, wherein the processor is configured to:
   reduce an amplitude of a DC component, which shows a zero frequency in at least one axial direction on the first image, on the second image, compared to other components.

5. The tomographic image forming apparatus according to claim 1, wherein the processor is configured to:
   reduce an amplitude of a frequency component, which is in a region having a predetermined width in an axis direction corresponding to the first axis or the second axis of the first image, on the second image, compared to other components.

6. The tomographic image forming apparatus according to claim 4, wherein the processor is configured to:
   reduce an amplitude of a frequency component, which is in a region having a predetermined width from the first axis or the second axis DC component of the first image, on the second image, compared to other components.

7. The tomographic image forming apparatus according to claim 6, comprising:
   a filter having a distribution in which amplitudes in both ends of the predetermined width from the DC component are approximated to original values.

8. The tomographic image forming apparatus according to claim 3, wherein the processor is configured to:

decrease the amplitude of the DC component to zero or smaller, or gradually approximate the amplitude of the DC component to zero.

9. The tomographic image forming apparatus according to claim 1, wherein the processor is configured to:
reduce noise on the third image by applying a filter thereto or performing a threshold process thereon.

10. The tomographic image forming apparatus according to claim 1, wherein the processor is configured to:
reduce noise on the third image by converting the third image into a frequency domain and applying a filter thereto or performing a threshold process thereon.

11. The tomographic image forming apparatus according to claim 1, wherein the processor is configured to:
select a predetermined region of an original image in which the line data is arranged in the direction of the second axis;
reduce an amplitude of a DC component, which shows a zero frequency in the direction of the second axis on the original image, on an image obtained by converting the image in the predetermined region into a frequency domain, compared to other components; and
replace the predetermined region of the original image with an image obtained by inversely converting the image into an image in the spatial domain,
wherein the image obtained is the first image.

12. The tomographic image forming apparatus according to claim 11,
wherein the image in the predetermined region is an image where a region other than the predetermined region of the original image is set to have the lowest brightness value, and
the processor is configured to:
extract the predetermined region from the image obtained by inversely converting the image into the spatial domain, and replaces the image in the predetermined region of the original image.

13. The tomographic image forming apparatus according to claim 11, wherein the processor is configured to:
select a region within a predetermined distance from the shallowest position of the first axis on the original image, as the predetermined region.

14. The tomographic image forming apparatus according to claim 11, wherein the processor is configured to:
select a region designated by a user as the predetermined region.

15. The tomographic image forming apparatus according to claim 1,
wherein brightness correction is performed after at least one filtering in the filtering processes.

16. A control method of a tomographic image forming apparatus which divides light output from a light source inside the apparatus into measurement light and reference light, and which generates a cross-sectional image of an imaging target based on light intensity of interference light obtained from reflected light obtained by emitting the measurement light to the imaging target and the reference light, the control method comprising:

generating a second image by converting into a frequency domain a first image in which line data being generated based on the light intensity and having information in a direction of a first axis showing a depth direction of the imaging target is arranged in a direction of a second axis;
removing or reducing an artifact by performing filtering on the second image; and
generating a third image by inversely converting the second image into a spatial domain.

17. The control method according to claim 16, wherein the first image is converted into the second image by Fourier transform, cosine transform, or sine transform.

18. The control method according to claim 16, comprising:
reducing an amplitude of a DC component which shows a zero frequency on the second image, compared to other components;
reducing an amplitude of a DC component, which shows a zero frequency in at least one axial direction on the first image, on the second image, compared to other components;
reducing an amplitude of a frequency component, which is in a region having a predetermined width in an axis direction corresponding to the first axis or the second axis of the first image, on the second image, compared to other components; and/or
reducing an amplitude of a frequency component, which is in a region having a predetermined width from the first axis or the second axis DC component of the first image, on the second image, compared to other components.

19. The control method according to claim 18, comprising:
applying a filter having a distribution in which amplitudes in both ends of the predetermined width from the DC component are approximated to original values.

20. A non-transitory computer readable medium for a tomographic image forming apparatus which divides light output from a light source inside the apparatus into measurement light and reference light, and which generates a cross-sectional image of an imaging target based on light intensity of interference light obtained from reflected light obtained by emitting the measurement light to the imaging target and the reference light, the non-transitory computer readable medium having instructions operable to cause one or more processors to perform operations comprising:
generating a second image by converting into a frequency domain a first image in which line data being generated based on the light intensity and having information in a direction of a first axis showing a depth direction of the imaging target is arranged in a direction of a second axis;
removing or reducing an artifact by performing filtering on the second image; and
generating a third image by inversely converting the second image into a spatial domain.

* * * * *